US008404259B2

(12) United States Patent
Welshimer et al.

(10) Patent No.: US 8,404,259 B2
(45) Date of Patent: Mar. 26, 2013

(54) DISPERSIBLE GRANULAR SUBSTRATE FOR PESTICIDE DELIVERY

(75) Inventors: James W. Welshimer, Findlay, OH (US); Timothy D. Birthisel, Perrysburg, OH (US)

(73) Assignees: The National Lime and Stone Co., Findlay, OH (US); The Andersons, Inc., Maumee, OH (US)

( * ) Notice: Subject to any disclaimer, the term of this patent is extended or adjusted under 35 U.S.C. 154(b) by 1060 days.

(21) Appl. No.: 11/546,035

(22) Filed: Oct. 10, 2006

(65) Prior Publication Data

US 2007/0082821 A1    Apr. 12, 2007

Related U.S. Application Data

(60) Provisional application No. 60/725,266, filed on Oct. 11, 2005.

(51) Int. Cl.
  *A01N 25/00* (2006.01)
  *A01N 25/08* (2006.01)
  *A01N 25/24* (2006.01)
  *A01N 47/10* (2006.01)
  *A01N 53/10* (2006.01)

(52) U.S. Cl. .......... 424/405; 504/367; 424/410

(58) Field of Classification Search ........ 504/367; 514/479, 531; 424/410, 405
See application file for complete search history.

(56) References Cited

U.S. PATENT DOCUMENTS

| | | | |
|---|---|---|---|
| 4,015,973 A | 4/1977 | Perrine | |
| 4,123,556 A * | 10/1978 | Karrer | 514/719 |
| 4,874,786 A | 10/1989 | Menconi | |
| 4,954,134 A | 9/1990 | Harrison | |
| 5,019,564 A * | 5/1991 | Lowe et al. | 514/75 |
| 5,078,779 A | 1/1992 | Van de Walle | |
| 5,228,895 A | 7/1993 | Kelly | |
| 5,242,690 A | 9/1993 | Moechnig | |
| 5,498,384 A | 3/1996 | Volk | |
| 5,830,512 A * | 11/1998 | Vrba | 424/724 |
| 6,231,660 B1 * | 5/2001 | Welshimer et al. | 106/405 |
| 6,613,138 B2 * | 9/2003 | Welshimer et al. | 106/405 |
| 2005/0175577 A1 * | 8/2005 | Jenkins et al. | 424/76.1 |
| 2005/0220885 A1 * | 10/2005 | Gilo et al. | 424/489 |
| 2006/0121075 A1 | 6/2006 | Gilo | |

FOREIGN PATENT DOCUMENTS

WO    WO 90/12503    * 11/1990

OTHER PUBLICATIONS

Goss, G.R., Taylor, D.R., and Kelley, W.B., "Granular Pesticide Formulations,"Pesticide Formulations and Application Systems: 15th Volume, ASTM STP 1268, Herbert M. Collins, Franklin R. Hall, and Michael Hopkinson, Eds., American Society for Testing and Materials, Philadelphia, 1994.*

* cited by examiner

*Primary Examiner* — Fereydoun G Sajjadi
*Assistant Examiner* — Courtney Brown
(74) *Attorney, Agent, or Firm* — Marshall & Melhorn, LLC

(57) ABSTRACT

An inert dispersible granular substrate is suitable for use as a carrier for chemical agents. The granular substrate is comprised of one or more mineral components, the one or more mineral components having a bulk density of greater than about 70 pounds per cubic foot, one or more dispersibility additives; and one or more water soluble binders. The granular substrate has a bulk density of from greater than 55 pounds pcf to about 70 pcf, a water dispersibility of less than 5 minutes, a pH of from 6 to 8, and sufficient strength to survive formulation processing after 3 days of continuous exposure to a temperature of approximately 75° F. and a relative humidity of approximately 95%. Preferably, an active pesticide is applied to the dispersible granular substrate. The water dispersible granular substrates may be produced by forming a granular substrate admixture, pelletizing the admixture to form granular substrates, and drying the granular substrates.

27 Claims, No Drawings

DISPERSIBLE GRANULAR SUBSTRATE FOR PESTICIDE DELIVERY

RELATED APPLICATION

This application is claiming the benefit, under 35 U.S.C. §119(e), of the provisional application filed Oct. 11, 2005 under 35 U.S.C. §111(b), which was granted Ser. No. 60/725, 266. This provisional application is hereby incorporated by reference.

BACKGROUND OF THE INVENTION

This invention relates to a dispersible granular substrate suitable for use as a carrier for chemical agents, as well as a method for producing a granular substrate. More particularly, this invention relates to a medium weight dispersible granular substrate.

Generally, granular substrates are utilized as carriers for active chemical agents, such as for example herbicides or other pesticides. The terms "pesticide" or "pesticides" are used herein in the broad sense that includes herbicides. The carriers, with the active chemical agents, are utilized to distribute the active agent over a broad area. The carriers are generally inert compounds that, upon application, break down over time.

Existing water soluble granular substrates are nutrient-based carriers, conventionally formed of ammonium sulfate. However, ammonium sulfate acts as a fertilizer, providing a growth response that may not be desired, and can burn turf if misapplied or applied at high rates as, for example, a mound treatment for ant control.

In addition, conventional granular substrates often have a tendency to break apart, thus creating handling and distribution problems. Granular substrates that resist attrition are preferred because they will not degrade and therefore maintain their particle size during handling. While resistance to attrition is important, in some applications it is preferable that the carrier compound breakdown or disintegrate upon exposure to water.

SUMMARY OF THE INVENTION

The invention is a dispersible granular substrate suitable for use as a carrier for chemical agents. The granular substrate is comprised of one or more mineral components, the one or more mineral components having a bulk density of greater than about 70 pounds per cubic foot, one or more dispersibility additives; and one or more water soluble binders. The granular substrate has a bulk density of from greater than 55 pounds pcf to about 70 pcf, a water dispersibility of less than 5 minutes, a pH of from 6 to 8, and sufficient strength to survive formulation processing after 3 days of continuous exposure to a temperature of approximately 75° F. and a relative humidity of approximately 95%. Preferably, an active pesticide is applied to the dispersible granular substrate.

According to another aspect of the invention, water dispersible granular substrates may be produced by forming a granular substrate admixture by mixing one or more mineral components, the one or more mineral components having a bulk density greater than about 70 pounds pcf, one or more dispersibility additives, and one or more water soluble binders. The admixture is then pelletized to form granular substrates. The granular substrates are dried at a temperature sufficient to remove excess moisture and produce finished granular substrates that have a bulk density of from greater than 55 pounds pcf to about 70 pcf and a water dispersibility of less than 5 minutes.

DESCRIPTION OF THE INVENTION

In accordance with the present invention, there is provided a dispersible granular substrate composition that is suitable for use as a carrier for active chemical agents. The present invention also includes a method for forming the dispersible granular substrate.

The dispersible granular substrate of the invention closely matches the density and "spreadability" of ammonium sulfate, but is "inert" in the sense that it does not contain a significant amount of plant nutrients and thus does not provide a growth response, is less hygroscopic, is not phytotoxic, and exhibits good chemical and physical stability. The dispersible granular substrate preferably has a pH of from 6 to 8, most preferably from 6.5 to 7.5, to provide a substrate with minimal reactivity.

Further, the dispersible granular substrate of the invention does not degrade during handling but preferably breaks down when exposed to moisture or water. The resistance to attrition ensures the proper distribution of the active chemical agent upon application. The ability to disintegrate upon exposure to water is preferred to provide the active chemical agent to the soil.

The dispersible granular substrate composition of the present invention includes one or more mineral components, one or more dispersibility additives, and one or more water soluble binders. The mineral component in the granular substrate is preferably one or more selected from the group consisting of dolomite and limestone. The mineral components make up about 65 wt % or more of the dispersible granular substrate. In general, the mineral components have a sizing of 100% passing through a 30 mesh screen and 50% or more passing through a 200 mesh screen. The mineral components have a preferred sizing of about 100% through a 50 mesh screen and 80% or more through a 200 mesh screen. The noted mesh sizes and all those mentioned hereafter conform with U.S. standard sieve sizes. Additionally, the mineral components have a bulk density of greater than about 70 pounds per cubic foot, and preferably have a bulk density of about 75 to about 90 pounds per cubic foot. The sizing of the mineral components may vary with respect to other ingredients utilized in the agglomerated substrate. In addition to the preferred mineral components, other stone or mineral dust compounds conforming with the size and bulk density parameters may be suitable for use with the present invention.

One or more dispersibility additives are utilized with the present inventive composition. The granular substrates of the invention include about 0.5 wt % to about 25 wt % of such additives, preferably from about 1 to 2 wt %. The dispersibility additives are generally inert compounds preferably having, in the case of solid dispersibility additives, a sizing of at least 20% passing through a 40 mesh screen. It is preferred that any solid dispersibility additives have a sizing of 100% passing through a 40 mesh screen. Additionally, the dispersibility additive(s) should be a non-fibrous material as indicated by the sizing parameters. Fibrous material can adversely impact the dispersibility and the flow characteristics of the finished granular substrate. The dispersibility additives are preferably one or more selected from the group consisting of expanded silica, fly ash, hydrated lime, wood flour, wood particle board flour, distiller's dried grain, thin stillage, ground wheat straw, cellulose, glycerins, glycols, cellulose, clay, soy flour, and mineral oil. However, other inert compounds providing the desired dispersibility and flow characteristics to the finished granular substrate may be suitable for use in the present inventive composition.

A preferred embodiment includes the use of wood flour resulting from finely milled wood particle board. The wood particle board typically contains approximately 10 wt % of a urea-formaldehyde resin. Another preferred embodiment includes the use of wheat straw flour resulting from finely milled wheat straw particle board. The wheat straw particle board contains a diphenylmethane diisocyanate resin. In both cases, the additional resin may assist in producing a granular substrate that does not degrade during handling but breaks down upon exposure to water.

A binder is utilized to agglomerate the ingredients of the present invention. In these embodiments, the binder is utilized at an amount up to about 20 wt % (dry basis) of the granular composition. The preferred amount of binder is generally 2 wt % to 20 wt %. The binder utilized will bind the ingredients into granular substrates which resist attrition, will not degrade and therefore maintain their particle size during handling. The binder is such that the resulting granular substrate has a resistance to attrition (RTA) value, in accordance with ASTM E 728-91 Volume 11.04, of at least 85%, preferably at least 90%. In addition, the selected binder needs to be sufficiently water soluble that the resulting granular substrate disperses quickly in water.

The binder is preferably selected from the group consisting of brewers condensed solubles, fermentation solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, citrus residium, cellulose derivatives, hemicellulose extract (such as the Temulose hemicellulose extract from Temple-inland Forest Products Division of Dibold, Tex.), urea liquor, or cellulose based polymer binders. The preferred binder is calcium lignosulfonate, such as the calcium lignosulfonates available from Flambeau River Papers, Inc. of Park Falls, Wis. Most preferred is the Ca Lignin available from Flambeau River Papers, Inc. that has been desugared.

Other water soluble binders having equivalent properties to, for example, the brewers condensed solubles, may be suitable for use in the present inventive composition, although economics may mitigate against their use.

The binder is generally added to the composition as a solution. The solution is typically provided as a water based slurry having about 40% to 50% solids by weight and weighing about 10 pounds per gallon. The binder may also be added as a powder and mixed with the other dry ingredients, subsequently mixing in an amount of water.

The composition of the present invention is generally produced by first creating an admixture of the noted components within the specified ranges. The mixing of the components may occur in either a batch or continuous mixing process. Conventional mixing devices are suitable for use with the present invention. The components should be thoroughly mixed at conditions which prevent degradation or compaction of the materials. During the mixing step, the binder composition is generally added to the mixture as a solution. Optionally, at least part of the water soluble binder may be added to the pelletizing apparatus during pelletizing. Additional water, up to about 15% by weight, may be necessary for agglomeration of the materials in the inventive composition.

The admixture is then fed into a pelletizing apparatus to produce the dispersible granular substrate of the present invention. Conventional pelletizing equipment is suitable for use in producing the substrate in pellet form. The preferred pelletizing equipment is a pelletizing pan. Additionally, drum granulators or other types of granulation equipment may be used to produce the granular substrate of the present invention.

Water may be added to the mixture during the pelletizing step of the process to assist in granulation of the material. The water is generally added at an amount which results in no greater than 35% by weight in the substrate.

In accordance with the present invention, the operation of a pelletizing pan may vary with the specific formulation or ingredients in order to produce a granular substrate with the preferred properties. For example, feed rates and locations of the admixture or the water, the angle of the pan, the speed of rotation of the disc, or the depth of the pan may be varied to produce the desired product. One skilled in the art of pelletizing is capable of recognizing the variables and making adjustments to obtain the granular substrate in pellet form.

The dispersible granular substrate may then be dried to a temperature of about 240° F. to about 300° F. to remove excess water utilized during the agglomeration of the components. The pellet is preferably dried to a total moisture content of 8% or less in accordance with ASTM standard D 5033 Volume 11.04. The substrates have a preferred total moisture content of 2.0% or less, more preferably 1.25% or less. The upper temperature limitation during the drying step prevents the degradation or burning of the organic binder in the granular substrate. The substrates may be dried in conventional drying units, such as for example a fluid bed dryer or a rotary dryer.

The resulting granular substrates are then screened to remove oversized and undersized granular substrates. The improperly sized material may be recycled to the mixing stage or milled to the appropriate size and rescreened.

The dispersible granular substrates of the invention have a bulk density, as measured by ASTM E 727 Volume 11.04 standards, of from greater than 55 pounds per cubic foot ("pcf") to about 70 pcf, preferably from about 57 pcf to about 67 pcf, more preferably from about 59 pcf to about 65 pcf, and most preferably about 62 pcf.

The size of particles is determined by the size guide number/uniformity index system used in the fertilizer industry. The substrates of the present invention have a size guide number between 50 and 300, preferably between about 100 to about 230, and preferably have a uniformity index of at least 35, more preferably at least 40. The size guide number describes the relative particle size and is obtained by multiplying the average particle size, in millimeters, by 100. The uniformity index is a comparison of large particles to small particles. The index is expressed as a whole number between 1 and 100 with higher numbers indicating better uniformity and tighter size range. Additionally, the sizing may be determined in accordance with ASTM E 728-91 Volume 11.04 wherein the sizing is preferably 20% or more passing through a 14 mesh screen and retained on a 40 mesh screen.

The dispersible granular substrate should be strong enough so that the particle does not significantly degrade during normal conveying and handling operations. The degradation of granular substrates would result in an increase in fine material which in turn would increase the bulk density. Additionally, dust or powder material absorbs more chemical agent and therefore would result in the improper distribution of the active chemical agent upon application.

It is preferred that the granular substrate not degrade until exposed to water. However, it is also important that the substrate not significantly degrade with high humidity. The ability of the granular substrate of the present invention to degrade with water is generally measured by means of a water dispersibility test. The test involves placing about 10 grams of the granular substrate into 100 ml of water at room temperature in a closed glass container. The container is then inverted and the time is observed until the material completely disperses. After every minute, the container is inverted. The granular substrate of the present invention has a dispersibility time of generally less than 5 minutes, preferably less than 3 minutes, and most preferably less than 1 minute.

It is further preferred that the granules of the invention exhibit better storability than conventional pelleted lime. In this regard, it is more specifically preferred that the granules maintain sufficient strength to survive formulation processing after at least 3 days, and more preferably 4 days for use in tropical climates, of continuous exposure to a temperature of approximately 75° F. and a relative humidity of approximately 95%. Sufficient strength may be determined by rolling the granules between the thumb and finger after the noted exposure. If the granules have a solid feel similar to dry pellets, then the assumption is that they would have sufficient strength to survive formulation processing, and they pass the storability test. But, if the pellets are mushy or soft and fall apart upon fingering, then they fail.

The strength of the granular substrate is determined through the crush strength test, ASTM E 382 Volume 3.06, and resistance to attrition (RTA) test, ASTM E 728-91 Volume 11.04. The dispersible granular substrate of the present invention has a crush strength between 2 and 8 pounds on an 8 mesh pellet. Additionally, in these embodiments, the granular substrate has an RTA value of at least 85%, more preferably at least 90%.

The granular substrates of the invention generally have a smooth surface and are spherical in shape. The spherocity lends to desired flow characteristics of the substrates in bulk form. The angle of repose is a test utilized to measure the ability of a substrate to flow in bulk form. The test is conducted on a 14×30 mesh sample. The granular substrates of the invention preferably have an angle of repose of 35 degrees or less.

The granular substrate should have the capability of absorbing the active chemical agent in order to function as a carrier. The active agent is generally absorbed in the carrier up to about five percent by weight. The substrate is also water soluble and therefore degrades upon exposure to moisture or water.

The dispersible granular substrate of the present invention is suitable for use as a carrier for active chemical agents. For example, active chemical agents could include herbicides or other pesticides that are commonly distributed through the use of a carrier in bulk form.

The following example, which constitutes the best mode presently contemplated by the inventors for practicing the present invention, is presented solely for the purpose of further illustrating and disclosing the present invention, and is not to be construed as a limitation on the invention. All percentages used herein are weight percentages unless specifically stated otherwise.

EXAMPLE

The dry based materials, wood particle board flour and dolomitic limestone powder, were thoroughly mixed in a ribbon type mixer before adding the binder composition. The binder composition, composed of calcium lignosulfonate in solution form, was added to the dry materials and then mixed in a pin mixer or turbulator.

The resulting wet mixture was then fed into a rotating pelletizing pan. The substrates, in pellet form, were transported from the pelletizing pan to a vibrating fluid bed dryer where the granular substrates were heated to remove excess water.

The finished granular substrates contained 1.2% wood particle board flour, 7.6% calcium lignosulfonate solids, and 90.6% dolomitic limestone powder, with 0.6% moisture being assumed. The granular substrates had an SGN of 140, a Uniformity Index ("UI") of 40, a bulk density of 64 pcf, an RTA of 94%, pH of 7.9, and a dispersibility of less than 1 minute.

Due to the wood particle board flour in the composition, the finished granular substrate provides a kinetic energy release upon exposure to moisture, as the swelling of the wood flour tears the granule apart. The granules of the invention also exhibit better storability than conventional pelleted lime, and enhanced resistance to attrition and storability.

In accordance with the provisions of the patent statutes, the present invention has been described in what is considered to represent its preferred embodiment. However, it should be noted that the invention can be practiced otherwise than as described without departing from its spirit and scope.

What is claimed is:

1. An inert dispersible granular substrate, suitable for use as a carrier for chemical agents, comprising a plurality of pellets, each pellet being formed of a mixture comprising:
   (a) one or more mineral components selected from the group consisting of dolomite and limestone, the one or more mineral components having a bulk density of greater than 70 pounds per cubic foot (pcf) and making up 65 wt % or more of the mixture;
   (b) one or more dispersibility additives; and
   (c) one or more water soluble binders;
   the granular substrate having a bulk density of from greater than 55 pcf to about 70 pcf.

2. The inert dispersible granular substrate as recited in claim 1, wherein the granular substrate has a bulk density of from about 57 pcf to about 67 pcf.

3. The inert dispersible granular substrate as recited in claim 1, wherein the granular substrate has a bulk density of from about 59 pcf to about 65 pcf.

4. The inert dispersible granular substrate as recited in claim 1, wherein said granular substrate has an RTA of at least 85%.

5. The inert dispersible granular substrate as recited in claim 1, wherein said granular substrate has an RTA of at least 90%.

6. The inert dispersible granular substrate as recited in claim 1, wherein said the one or more mineral components have a bulk density of from about 75 to about 90 pounds per cubic foot.

7. The inert dispersible granular substrate as recited in claim 1, wherein said granular substrate has a water dispersibility of less than 3 minutes.

8. The inert dispersible granular substrate as recited in claim 1, wherein said granular substrate has a water dispersibility of less than 1 minute.

9. The inert dispersible granular substrate as recited in claim 1, wherein said granular substrate has a particle size guide number of about 50 to about 300 and a uniformity index of at least 35.

10. The inert dispersible granular substrate as recited in claim 1, wherein said granular substrate has a particle size guide number of about 100 to about 230 and a uniformity index of at least 40.

11. The inert dispersible granular substrate as recited in claim 1, wherein said granular substrate has a total moisture content of 8% or less.

12. The inert dispersible granular substrate as recited in claim 1, wherein said granular substrate has an angle of repose of 35 degrees or less.

13. The inert dispersible granular substrate as recited in claim 1, wherein said dispersibility additive is one or more of the group consisting of expanded silica, fly ash, hydrated lime, wood flour, wood particle board flour, distiller's dried grain, thin stillage, ground wheat straw, cellulose, glycerins, glycols, clay, soy flour, and mineral oil.

14. The inert dispersible granular substrate as recited in claim 1, wherein said dispersibility additive is wood flour containing an amount of urea-formaldehyde resin.

15. The inert dispersible granular substrate as recited in claim 1, wherein said mineral component is dolomite.

16. The inert dispersible granular substrate as recited in claim 1, wherein said water soluble binder is one or more of the group consisting of brewers condensed solubles, fermentation solubles, lignosulfonate, sodium carbonate lignin, cane molasses, beet syrup, beet molasses, desugared beet molasses, whey, starch, soy solubles with cane molasses or the like, hydrolyzed collagen, amino acid solutions, citrus residium, cellulose derivatives, hemicellulose extract, urea liquor, or cellulose based polymer binders.

17. The inert dispersible granular substrate as recited in claim 1, wherein the granular substrate has a strength such that, at a nominal particle size of 8 mesh, the granular substrate has a crush strength between 2 and 8 pounds.

18. The inert dispersible granular substrate as recited in claim 1 having sufficient strength to survive formulation processing after 4 days of continuous exposure to a temperature of approximately 75° F. and a relative humidity of approximately 95%.

19. The inert dispersible granular substrate as recited in claim 1 having a pH of from 6.5 to 7.5.

20. The inert dispersible granular substrate as recited in claim 1, wherein the one or more mineral components have a sizing of about 100% passing through a 30 mesh screen and about 50% or more passing through a 200 mesh screen.

21. A method of producing water dispersible granular substrates, comprising:

(a) mixing one or more mineral components selected from the group consisting of dolomite and limestone, the one or more mineral components having a bulk density greater than 70 pounds per cubic foot (pcf), one or more dispersibility additives, and one or more water soluble binders to form a granular substrate admixture, the one or more mineral components making up 65 wt % or more of the admixture;

(b) pelletizing the admixture to form granular substrates; and (c) drying the granular substrates at a temperature sufficient to remove excess moisture and produce finished granular substrates having a bulk density of from greater than 55 pcf to about 70 pcf and a water dispersibility of less than 5 minutes.

22. A method as recited in claim 21, further comprising exposing the granular substrates to one or more active chemical agents such that the granular substrates absorb an effective amount of the one or more active chemical agents.

23. A granular pesticide comprising:

(a) an inert dispersible granular substrate comprised of a plurality of pellets, each pellet being formed of a mixture comprising:

(i) one or more mineral components selected from the group consisting of dolomite and limestone, the one or more mineral components having a bulk density of greater than 70 pounds per cubic foot (pcf);

(ii) one or more dispersibility additives; and (iii) one or more water soluble binders;

the one or more mineral components making up 65 wt % or more of the granular substrate; and (b) an active pesticide applied onto the dispersible granular substrate;

the granular pesticide having a bulk density of from greater than 55 pcf to about 70 pcf and a water dispersibility of less than 5 minutes.

24. The method of claim 21, wherein the one or more mineral components make up 90 wt % or more of the admixture.

25. The granular pesticide of claim 23, wherein the one or more mineral components make up 90 wt % or more of the granular substrate.

26. The inert dispersible granular substrate of claim 1, wherein the one or more mineral components make up 90 wt % or more of the mixture.

27. The inert dispersible granular substrate of claim 1 having a water dispersibility of less than 5 minutes, a pH of from 6 to 8, and sufficient strength to survive formulation processing after 3 days of continuous exposure to a temperature of approximately 75° F. and a relative humidity of approximately 95%.

* * * * *